(12) United States Patent
Couture et al.

(10) Patent No.: US 12,260,561 B2
(45) Date of Patent: Mar. 25, 2025

(54) TRACKING SYSTEM FOR ROBOTIZED COMPUTER-ASSISTED SURGERY

(71) Applicant: ORTHOSOFT ULC, Montreal (CA)

(72) Inventors: Pierre Couture, Montreal (CA); Louis-Philippe Amiot, Montreal (CA); Alain Richard, Lachine (CA); Karine Duval, Montreal (CA); Bruno Andre, Montreal (CA); Delphine Cirette, Montreal (CA); Yann Zimmermann, Montreal (CA); Ronan Lacour, Montreal (CA)

(73) Assignee: ORTHOSOFT ULC, Montreal (CA)

( * ) Notice: Subject to any disclaimer, the term of this patent is extended or adjusted under 35 U.S.C. 154(b) by 521 days.

(21) Appl. No.: 17/841,069

(22) Filed: Jun. 15, 2022

(65) Prior Publication Data

US 2022/0398744 A1 Dec. 15, 2022

Related U.S. Application Data

(60) Provisional application No. 63/210,688, filed on Jun. 15, 2021.

(51) Int. Cl.
*G06T 7/20* (2017.01)
*A61B 34/20* (2016.01)
(Continued)

(52) U.S. Cl.
CPC .............. *G06T 7/20* (2013.01); *A61B 34/20* (2016.02); *A61B 34/30* (2016.02); *B25J 13/088* (2013.01);
(Continued)

(58) Field of Classification Search
CPC .......... G06T 7/20; G06T 7/0012; G06T 7/30; G06T 2207/10132; G06T 2207/30008; A61B 34/20; A61B 34/30; A61B 2034/2063; A61B 17/154; A61B 17/74; A61B 90/361; A61B 2034/2055; A61B 2034/2059; A61B 2090/0818;
(Continued)

(56) References Cited

U.S. PATENT DOCUMENTS

| | | | | |
|---|---|---|---|---|
| 9,901,405 | B2 * | 2/2018 | Valin | A61B 34/20 |
| 2007/0156157 | A1 * | 7/2007 | Nahum | A61B 34/76 |
| | | | | 606/130 |

(Continued)

*Primary Examiner* — Juan A Torres
(74) *Attorney, Agent, or Firm* — NORTON ROSE FULBRIGHT CANADA LLP

(57) ABSTRACT

A system for tracking at least one object in computer-assisted surgery may include a processing unit and a non-transitory computer-readable memory communicatively coupled to the processing unit and comprising computer-readable program instructions executable by the processing unit for: obtaining orientation data from at least one inertial sensor unit on at least one object; concurrently obtaining position and orientation data for a robot arm relative to a frame of reference; registering the at least one object with the robot arm to determine a position of the at least one object in the frame of reference; and continuously tracking and outputting the position and orientation of the at least one object in the frame of reference, using the orientation data from the at least one inertial sensor unit on the at least one object and the position and orientation data for the robot arm.

20 Claims, 5 Drawing Sheets

(51) Int. Cl.
*A61B 34/30* (2016.01)
*B25J 13/08* (2006.01)
*G06T 7/00* (2017.01)
*G06T 7/30* (2017.01)
*G06T 7/70* (2017.01)

(52) U.S. Cl.
CPC .............. *G06T 7/0012* (2013.01); *G06T 7/30* (2017.01); *G06T 7/70* (2017.01); *A61B 2034/2063* (2016.02); *G06T 2207/10132* (2013.01); *G06T 2207/30008* (2013.01)

(58) Field of Classification Search
CPC ...... A61B 2090/365; A61B 2090/3937; A61B 2034/105; A61B 2034/2048; B25J 13/088
USPC ......................................................... 382/128
See application file for complete search history.

(56) References Cited

U.S. PATENT DOCUMENTS

| | | | |
|---|---|---|---|
| 2007/0219559 A1* | 9/2007 | Heavener | A61B 17/1764 606/87 |
| 2008/0004633 A1* | 1/2008 | Arata | A61B 34/20 606/130 |
| 2008/0234664 A1* | 9/2008 | May | A61B 17/17 606/1 |
| 2009/0043344 A1* | 2/2009 | Schlotterback | A61F 2/30756 604/509 |
| 2009/0048597 A1* | 2/2009 | Heavener | A61B 34/10 606/53 |
| 2009/0076655 A1* | 3/2009 | Blondel | A61B 34/35 700/254 |
| 2011/0153076 A1* | 6/2011 | Noro | B25J 9/1664 700/245 |
| 2011/0208256 A1* | 8/2011 | Zuhars | A61F 2/30942 606/86 R |
| 2014/0163736 A1* | 6/2014 | Azizian | A61B 34/20 700/259 |
| 2017/0360512 A1* | 12/2017 | Couture | A61B 34/30 |
| 2017/0360513 A1* | 12/2017 | Amiot | A61B 34/20 |
| 2018/0132949 A1* | 5/2018 | Merette | G06T 11/60 |
| 2018/0214221 A1* | 8/2018 | Crawford | B25J 13/08 |
| 2018/0235715 A1* | 8/2018 | Amiot | A61B 34/10 |
| 2018/0353192 A1* | 12/2018 | Leveille | A61B 17/157 |
| 2019/0029759 A1* | 1/2019 | McDonell | A61B 34/20 |
| 2019/0053813 A1* | 2/2019 | Leveille | A61B 17/155 |
| 2020/0069372 A1* | 3/2020 | Dufour | A61B 34/10 |
| 2020/0078948 A1* | 3/2020 | Krause | G06F 3/0346 |
| 2020/0281667 A1* | 9/2020 | Blondel | A61B 8/4218 |

* cited by examiner

TRACKING SYSTEM FOR ROBOTIZED COMPUTER-ASSISTED SURGERY

CROSS-REFERENCE TO RELATED APPLICATION

The present application claims the priority of U.S. Patent Application No. 63/210,688 filed on Jun. 15, 2021, the contents of which are incorporated herein by reference.

TECHNICAL FIELD

The present application relates to bone and tool tracking in robotized computer-assisted surgery.

BACKGROUND OF THE ART

Tracking of surgical instruments or tools and bodily parts is an integral part of computer-assisted surgery (hereinafter "CAS"). The tools are tracked for position and/or orientation in such a way that information pertaining to bodily parts is obtained. The information is then used in various interventions (e.g., orthopedic surgery, neurological surgery) with respect to the body, such as bone alterations, implant positioning, incisions and the like during surgery.

The tracking technologies may use different technologies, such as mechanical, acoustical (ultrasound), magnetic, optical and radio frequency (RF) tracking. Depending on the technology used, different types of trackable members are fixed, permanently or temporarily, to the items that needs to be tracked. For instance, during Total Knee Replacement (TKR) surgery, trackable members are fixed to the limbs and to the different surgical instruments, and these trackable members are tracked by the tracking system. The CAS system calculates position and orientation data associated with the tracking, and the information displayed by the computer is used by the surgeon to visualize the position of the instrument(s) being manipulated with respect to the limbs, or in numerical values.

Optical tracking is commonly used in different forms. For example, passive retroreflective components are provided on tools and bones. In order to obtain values for position and/or orientation, the optical elements must be in the line of sight of the optical sensor device. One common constraint with optical tracking systems is the requirement for a line of sight between image acquisition devices stationary and the objects to track. A surgical procedure employing optical tracking may be imposed a given orientation as a function of the required visibility between the optical sensor apparatus and the optical elements. If the line of sight is disrupted, tracking may be paused, as a possible consequence. In automated robotic surgery, the interruption of optical tracking may result in the need for human intervention. There remains room for improvement.

SUMMARY

In accordance with an aspect of the present disclosure, there is a system for tracking at least one object in computer-assisted surgery, comprising: a processing unit; and a non-transitory computer-readable memory communicatively coupled to the processing unit and comprising computer-readable program instructions executable by the processing unit for: obtaining orientation data from at least one inertial sensor unit on at least one object; concurrently obtaining position and orientation data for a robot arm relative to a frame of reference; registering the at least one object with the robot arm to determine a position of the at least one object in the frame of reference; and continuously tracking and outputting the position and orientation of the at least one object in the frame of reference, using the orientation data from the at least one inertial sensor unit on the at least one object and the position and orientation data for the robot arm.

In accordance with another aspect of the present disclosure, there is provided a system for tracking at least one object in computer-assisted surgery, comprising: a processing unit; and a non-transitory computer-readable memory communicatively coupled to the processing unit and comprising computer-readable program instructions executable by the processing unit for: obtaining orientation data from at least one ultrasound imaging system connected to at least one object; concurrently obtaining position and orientation data for a robot arm relative to a frame of reference; registering the at least one object with the robot arm to determine a position of the at least one object in the frame of reference; and continuously tracking and outputting the position and orientation of the at least one object in the frame of reference, using the orientation data from the at least one ultrasound imaging system on the at least one object and the position and orientation data for the robot arm.

DETAILED DESCRIPTION

Figure 1:
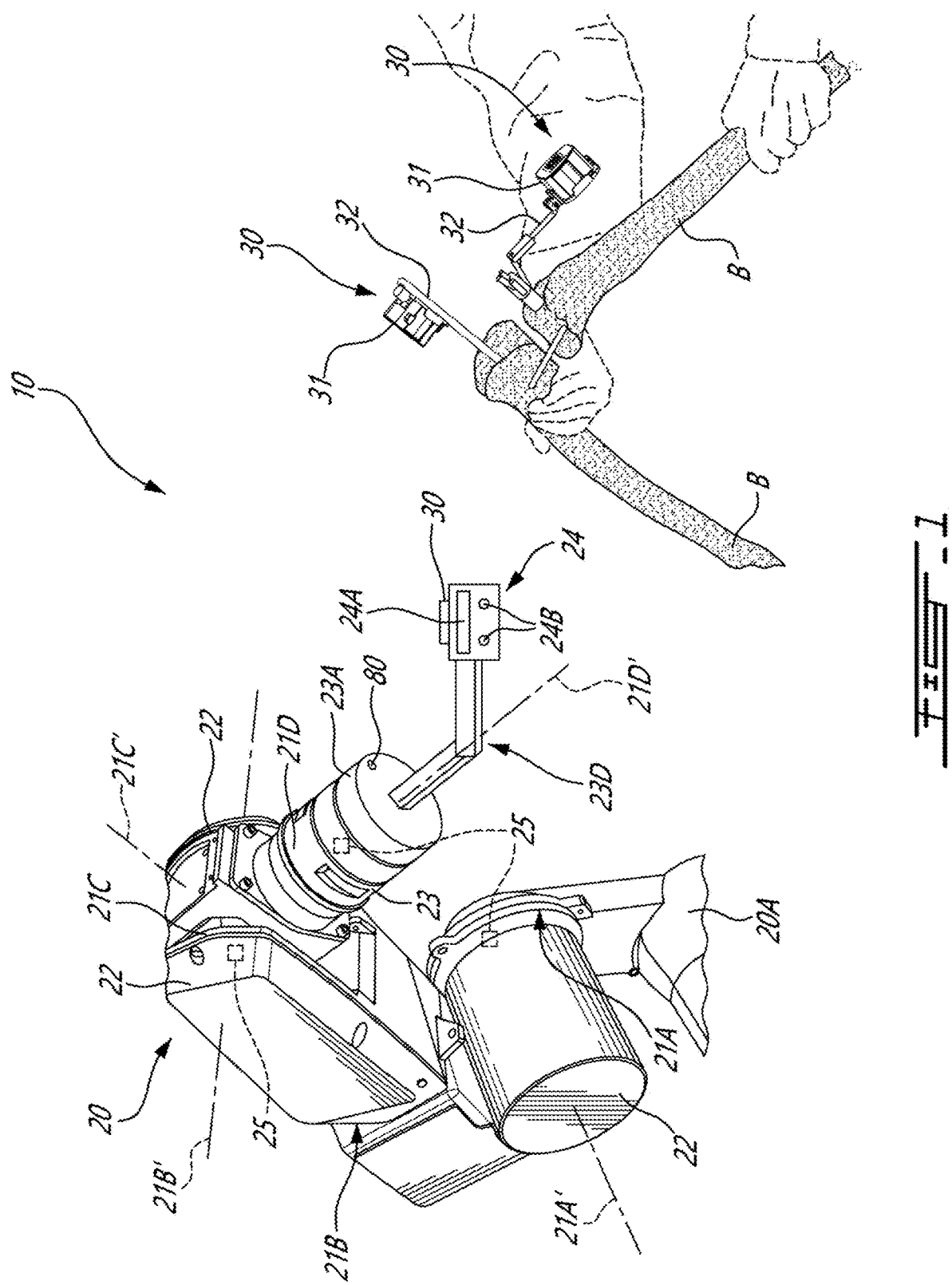
FIG. 1 is a schematic view of a tracking system for robotized computer-assisted surgery (CAS) in accordance with an aspect of the present disclosure.
Figure 2:
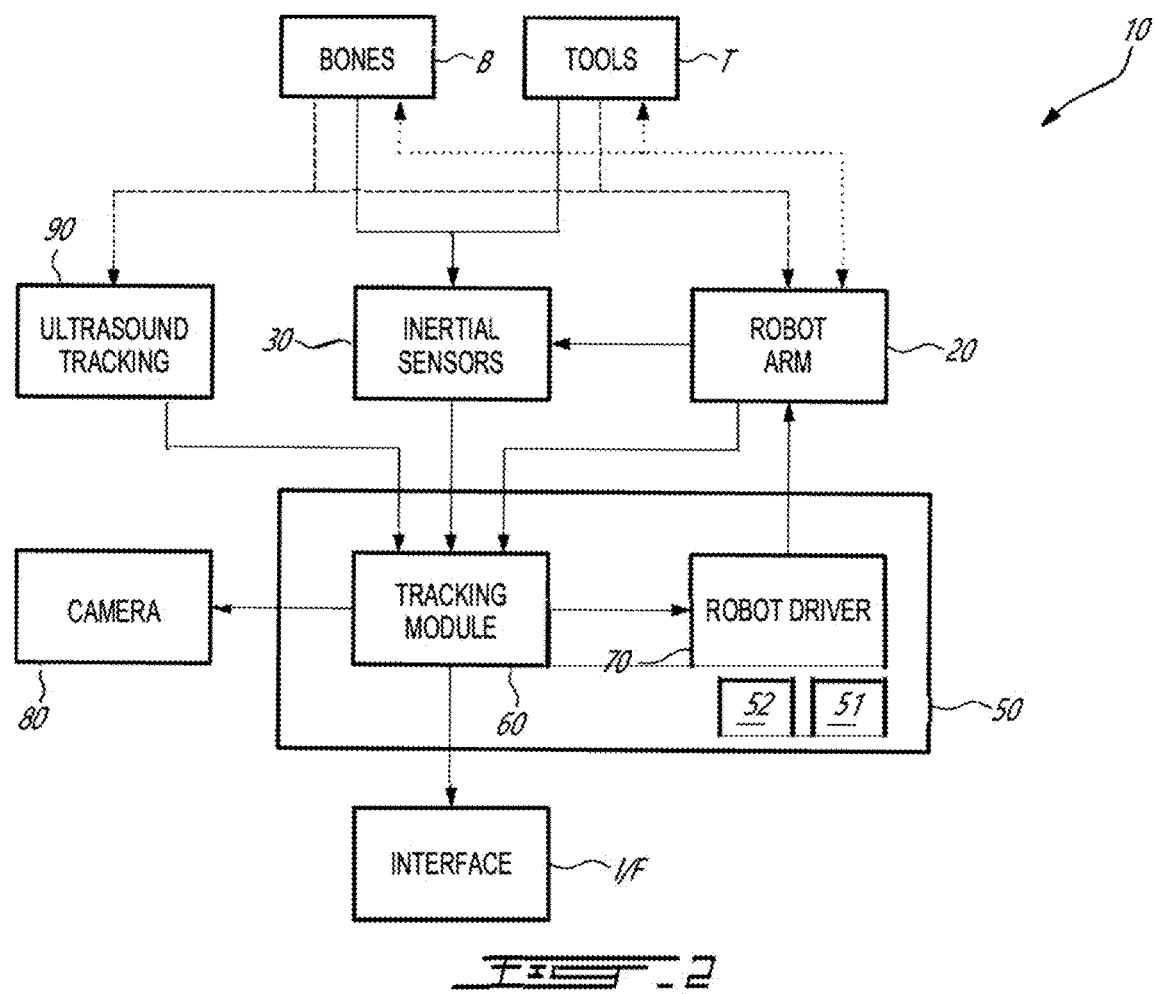
FIG. 2 is a block diagram of the tracking system for robotized computer-assisted surgery of FIG. 1.

Referring to FIGS. 1 and 2, a tracking system for robotized computer-assisted surgery (CAS) system is generally shown at 10, and is used to provide surgery assistance to an operator. In FIG. 1, the system 10 is shown relative to a dummy patient's knee joint in supine decubitus, but only as an example. The system 10 could be used for other body parts, including non-exhaustively hip joint, spine, and shoulder bones, for orthopedic surgery, but could also be used in other types of surgery.

The tracking system 10 may be robotized in a variant, and has, may have or may be used with a robot as shown by its one or more robot arms 20, one or more inertial sensor units 30, a CAS controller 50, a tracking module 60, and a robot driver 70, or any combination thereof:

The robot, shown by its robot arm 20 may optionally be present as the working end of the system 10, and may be used to perform or guide bone alterations as planned by an operator and/or the CAS controller 50 and as controlled by the CAS controller 50. The robot arm 20 may also be configured for collaborative/cooperative mode in which the operator may manipulate the robot arm 20. For example, the tooling end, also known as end effector, may be manipulated by the operator while supported by the robot arm 20. The robot arm 20 may be the coordinate measuring machine (CMM) of the tracking system 10;

The inertial sensor units 30 are positioned on the patient tissue (e.g., bones B), on the robot arm 20, and/or on the tool(s) T and surgical instruments, and provide tracking data for the bones or tools.

The CAS controller 50 includes the processor(s) and appropriate hardware and software to run a computer-assisted surgery procedure in accordance with one or more workflows. The CAS controller 50 may include or operate the tracking module 60, and/or the robot driver 70. As described hereinafter, the CAS controller 50 may also drive the robot arm 20 through a planned surgical procedure;

The tracking module 60 is tasked with determining the position and/or orientation of the various relevant objects during the surgery procedure, such as the bone(s) B and tool(s) T, using data acquired by the inertial sensor unit(s) 30 (e.g., angular rates of change) and by the robot arm 20, and/or obtained from the robot driver 70. The position and/or orientation may be used by the CAS controller 50 to control the robot arm 20;

The robot driver 70 is tasked with powering or controlling the various joints of the robot arm 20, based on operator demands or on surgery planning;

A camera 80 may be present, for instance as a complementary registration tool. The camera 80 may for instance be mounted on the robot 20, such as on the robot arm, such that the point of view of the camera 80 is known in the frame of reference. The camera 80 may be on its own stand as well;

An ultrasound imaging system 90 may optionally be part of the system 10, to contribute to the tracking of subcutaneous structures, such as the pelvis or other bones.

Other components, devices, systems, may be present, such as surgical instruments and tools T, interfaces I/F such as displays, screens, computer station, servers, and like etc. Secondary tracking systems may also be used for redundancy.

Referring to FIG. 1, the robot 20 (referred to herein as robot 20 or robot arm 20) may have the robot arm stand from a base, for instance in a fixed relation relative to the operating-room (OR) table supporting the patient, whether it is attached or detached from the table. The robot arm 20 has a plurality of joints 21 and links 22, of any appropriate form, to support a tool head 23 that interfaces with the patient. For example, the end effector or tool head may optionally incorporate a force/torque sensor for collaborative/cooperative control mode, in which an operator manipulates the robot arm 20. The robot arm 20 is shown being a serial mechanism, arranged for the tool head 23 to be displaceable in a desired number of degrees of freedom (DOF). For example, the robot arm 20 controls 6-DOF movements of the tool head, i.e., X, Y, Z in the coordinate system, and pitch, roll and yaw. Fewer or additional DOFs may be present. For simplicity, only a fragmented illustration of the joints 21 and links 22 is provided, but more joints 21 of different types may be present to move the tool head 23 in the manner described above. The joints 21 are powered for the robot arm 20 to move as controlled by the CAS controller 50 in the six DOFs, and in such a way that the position and orientation of the tool head 23 in the coordinate system may be known, for instance by readings from encoders on the various joints 21, or from any integrated rotational joint sensing enabling rotation of the joints 21 to be quantified. Therefore, the powering of the joints is such that the tool head 23 of the robot arm 20 may execute precise movements, such as moving along a single direction in one translation DOF, or being restricted to moving along a plane, among possibilities. Such robot arms 20 are known, for instance as described in U.S. patent application Ser. No. 11/610,728, and incorporated herein by reference. One of the inertial sensor unit 30 may be on the robot arm 20 for the tracking of the end effector of the robot arm 10. By way of example, robot arm 20 can include joint 21A that permits rotation about axis 21A', joint 21B that can permit rotation about axis 21B', joint 21C that can permit rotation about axis 21C' and joint 21D that can permit rotation about axis 21D'. Other distal joints and links may be present to assist in providing the required DOFs to the robot arm 20.

The tool head 23 of robot arm 20 may be defined by a chuck or like tool interface, typically actuatable in rotation. As a non-exhaustive example, numerous tools may be used as end effector for the robot arm 20, such tools including a registration pointer, a reamer (e.g., cylindrical, tapered), a reciprocating saw, a retractor, a laser rangefinder or light-emitting device (e.g., the indicator device of U.S. Pat. No. 8,882,777), laminar spreader depending on the nature of the surgery. The various tools may be part of a multi-mandible configuration or may be interchangeable, whether with human assistance, or as an automated process. The installation of a tool in the tool head may then require some calibration in order to track the installed tool in the X, Y, Z coordinate system of the robot arm 20.

As shown in FIG. 1, the tool head 23 of the robot arm 20 is illustrated as being a universal instrument adapter, which can be positioned by robot arm 20 relative to surgical area A in a desired orientation according to a surgical plan, such as a plan based on preoperative imaging. The universal instrument adapter may include a tool base 23A, an extension arm 23B, at the end of which a cutting guide 24 is located. The cutting guide 24 may be known as a cutting block, adapter block, etc. In an embodiment, the extension arm 23B may have a first segment and second segment, though fewer or more segments may be present, so as to give a given orientation to the cutting guide 24 relative to the tool head 23. The cutting guide 24 may have a body defining a guide surface 24A (e.g., cut slot), and pin holes 24B. In an example, the cutting guide 24 can be configured as a talus resection block for use in a total knee arthroplasty. Other configurations of the cutting guide 24 may be used, such as with or without pin holes 24B.

In order to position the cutting guide 24 or like end effector of the robot arm 20 relative to the patient B, the CAS controller 50 can manipulate the robot arm 20 automatically by the robot driver 70, or by a surgeon manually operating the robot arm 20 (e.g. physically manipulating, via a remote controller through the interface I/F) to move the end effector of the robot arm 20 to the desired location, e.g., a location called for by a surgical plan to align an instrument relative to the anatomy. Once aligned, a step of a surgical procedure can be performed, such as by using the cutting guide 24. For example, the cutting guide 24 may be secured to the bone B in the alignment using pins (e.g., Steinmann pins) in the pin holes 24B, for a cut blade to then be used as guide by the guide surface 24A.

The robot arm 20 may include sensors 25 in its various joints 21 and links 22. The sensors 25 may be of any appropriate type, such as rotary encoders, optical sensors, position switches, for the position and orientation of the end effector, and of the tool in the tool head 23 (e.g., cutting block 24) to be known. More particularly, the tracking module 60 may determine the position and orientation of the robot arm 20 in a frame of reference of the robot arm 20, such as by obtaining the position (x,y,z) and orientation (phi, theta, ro) of the tool from the robot driver 70 using the sensors 25 in the robot arm 20. Using the data from the sensors 25, the robot arm 20 may be the coordinate measuring machine (CMM) of the tracking system 10, with a frame of reference (e.g., coordinate system, referential system) of the procedure being relative to the fixed position of the base of the robot 20. The sensors 25 must provide the precision and accuracy appropriate for surgical procedures. The coupling of tools to the robot arm 20 may automatically cause a registration of the position and orientation of the tools in the frame of reference of the robot arm 20, though steps of calibration could be performed. For example, when the cutting guide 24 is coupled to the robot arm 20 such as in the example of FIG. 1, a position and orientation of the guide surface 24A may be registered for its subsequent tracking as the robot arm 20 moves in space. The geometry of the cutting guide 24 is thus known, as well as the manner by which the cutting guide 24 is coupled to the robot arm 20, to allow this automatic registration. Additional steps may be performed to register/calibrate the cutting guide 24, such as the contact with a probe, image processing, data entry, etc.

One of the inertial sensor units 30 may optionally be provided on the robot arm 20, such as on the end effector, on the tool head 23, on the cutting guide 24, etc. The orientation readings provided by the inertial sensor unit 30 on the robot arm 20 may be redundant relative to the embedded tracking of the robot arm 20, and may be used as described hereinbelow.

Referring to FIG. 1, the inertial sensor units 30 are shown secured to the bones B and to the robot arm 20, but may also or alternatively be on instruments. The inertial sensor unit 30 may be known as a sourceless sensor, a micro-electromechanical sensor unit (MEMS unit), and has any appropriate set of inertial sensors (e.g., accelerometers and/or gyroscope) to produce tracking data in at least three degrees of rotation (i.e., the orientation about a set of three axes is tracked). The sensor unit 30 may be self-enclosed in a pod 31, as shown, that may be connectable in an accurate and predetermined manner to a bone, an instrument, the robot arm 20. For example, connectors 32 are used to immovably anchor the inertial sensor units 30 to the bones. As observed, the connector 32 may be a rod inserted in the intramedullary canal at the entry point of the mechanical axis of the knee femur. The connectors 32 may integrate additional features, such as a cut guide with varus-valgus adjustment capability, for example, in the form of dials, for example as described in U.S. Patent Application Publication No. 2019/0053813, incorporated herein by reference. The inertial sensor units 30 may include a processor and a non-transitory computer-readable memory communicatively coupled to the processor and comprising computer-readable program instructions executable by the processor. Moreover, the inertial sensor units 30 may be self-contained, in that they may be pre-calibrated for operation, have their own powering or may be connected to a power source, and may have an interface, such as in the form of a display thereon (e.g., LED indicators). Although not shown, additional inertial sensor units 30 may be present on the bone, for instance to digitize the mechanical axis of the bone.

Referring to FIG. 2, the CAS controller 50 is shown in greater detail relative to the other components of the robotized tracking system 10. The CAS controller 50 has a processor unit 51 and a non-transitory computer-readable memory 52 communicatively coupled to the processing unit 51 and configured for executing computer-readable program instructions executable by the processing unit 51 for to perform some functions, such as tracking the patient tissue and tools, using the position and orientation data from the robot 20 and the readings from the inertial sensor unit(s) 30. The CAS controller 50 may also control the movement of the robot arm 20 via the robot driver module 70. The tracking system 10 may comprise various types of interfaces I/F, for the information to be provided to the operator. The interfaces I/F may include and/or screens including wireless portable devices (e.g., phones, tablets), audio guidance, LED displays, head-mounted display for virtual reality, augmented reality, mixed reality, among many other possibilities. For example, the interface I/F comprises a graphic-user interface (GUI) operated by the system 10. The CAS controller 50 may also display images captured pre-operatively, or using cameras associated with the procedure (e.g., camera 80, laparoscopic cameras, tool mounted cameras), for instance to be used in the collaborative/cooperative control mode of the system 10, or for visual supervision by the operator of the system 10, with augmented reality for example. The CAS controller 50 may drive the robot arm 20, in performing the surgical procedure based on the surgery planning achieved pre-operatively. The CAS controller 50 may run various modules, in the form of algorithms, code, non-transient executable instructions, etc, in order to operate the tracking system 10 in the manner described herein. The CAS controller 50 may be part of any suitable processor unit, such as a personal computer or computers including laptops and desktops, tablets, server, etc.

The tracking module 60 may be a subpart of the CAS controller 50, or an independent module or system. The tracking module 60 receives the position and orientation data from the robot 20 and the readings from the inertial sensor unit(s) 30. The tracking module 60 may hence determine the relative position of the objects relative to the robot arm 20 in a manner described below. The tracking module 60 may also be provided with models of the objects to be tracked. For example, the tracking module 60 may track bones and tools, and hence may use virtual bone models and tool models. The bone models may be acquired from pre-operative imaging (e.g., MRI, CT-scans), for example in 3D or in multiple 2D views, including with 2D X-ray to 3D bone model technologies. The virtual bone models may also include some image processing done preoperatively, for example to remove soft tissue or refine the surfaces that will be exposed and tracked. The virtual bone models may be of greater resolution at the parts of the bone that will be tracked during surgery, such as the knee articulation in knee surgery. The bone models may also carry additional orientation data, such as various axes (e.g., longitudinal axis, mechanical axis, etc). The bone models may therefore be patient specific. It is also considered to obtain bone models from a bone model library, with the data obtained from the video images used to match a generated 3D surface of the bone with a bone from the bone atlas. The virtual tool models may be provided by the tool manufacturer, or may also be generated in any appropriate way so as to be a virtual 3D representation of the tool(s).

Additional data may also be available, such as tool orientation (e.g., axis data and geometry). By having access to bone and tool models, the tracking module 60 may obtain additional information, such as the axes related to bones or tools.

As the inertial sensor unit(s) 30 are secured to the bones or to the instruments, in immovable fashion, the bones or instruments may be tracked via the inertial sensor unit(s) 30, while also being visually tracked. Therefore, as the inertial sensor unit(s) 30 have a fixed geometry on the objects that are tracked, the readings from the inertial sensor unit 30 provide data on the orientation of the bone B or robot arm 20, such as three-axis of orientation. The inertial sensor unit 30 may not readily or rapidly provide positional tracking data, i.e., position in X,Y,Z. Consequently, the tracking module 60 may combine this orientation tracking data to the position and orientation data from the sensors 25 embedded in the robot arm 20, in which case the positional tracking data for the objects may be calculated by the tracking module 60, as detailed below. Therefore, the combination by the tracking module 60 of the tracking from the robot arm 20 and that from the signals of the inertial sensor unit(s) 30 enable the tracking module 60 to track objects equipped solely with inertial sensor units 30 in both position and orientation, as explained below.

In an embodiment, the tracking module 60 uses the inertial sensor unit 30 on the bone B to obtain the orientation of the bone B in the coordinate system, and locates the bone B using other methods, such as obtaining the position and orientation of a probing tool from the robot driver 70 using the encoders or like sensors 25 in the robot arm 20, in a registration procedure described below.

Still referring to FIG. 2, the CAS controller 50 may have the robot driver 70, if a robot arm 20 is present in the tracking system 10. The robot driver 70 is tasked with powering or controlling the various joints of the robot arm 20. There may be some force feedback provided by the robot arm 20 to avoid damaging the bones. The robot driver 70 may perform actions based on a surgery planning. The surgery planning may be a module programmed specifically for any given patient, according to the parameters of surgery desired by an operator such as an engineer and/or surgeon. The parameters may include geometry of selected, planned bone cuts, planned cut depths, sequence or workflow of alterations with a sequence of surgical steps and tools, tools used, etc.

In an embodiment, additional tracking technology may be used, such as technologies relying on optical tracking, for instance via the camera 80. For example, the camera 80 may be a depth camera that captures footage that can be processed (i.e., image processing) using existing models of tracked objects (e.g., tools, bones) to locate them in the referential system. The camera 80 may also use tracking tokens to assist in the tracking. In a variant, the camera 80 may also rely on operating room fixtures for tracking, such fixtures being constellation references. For example, visual references may be mounted to a room wall or ceiling, and the camera 80 may use such visual references as datum. Such visual references may be in the line of sight of the camera 80 along with the objects being tracked. The position and orientation of the surgical tool calculated by the tracking module 60 using optical tracking may be redundant over the tracking data provided by the robot driver 70 and its embedded robot arm sensors 25, and inertial sensor unit(s) 30. However, the redundancy may assist in ensuring the accuracy of the tracking of the surgical tool. For example, the redundancy is used as a safeguard against incorrect tracking from the CAS controller 50, for instance due to relative movement between the robot arm 20 and the patient and/or table. Also, the tracking of the tool using the tracking module 60 may be used to detect any discrepancy between a calculated position and orientation of the surgical tool T through the sensors on the robot arm 20 and inertial sensor unit(s) 30, and the actual position and orientation of the surgical tool. For example, an improper mount of the tool T into the chuck of the robot arm 20 could be detected from the output of the tracking module 60, when verified by comparing the position and orientation from the robot driver 70 (e.g., obtained from the encoders on the robot arm 20) with the optical tracking. The operator may be prompted to verify the mount, via the interface I/F or head-mounted display 20. However, the tracking system 10 with tracking system may be employed without any optical tracking.

Figure 3:
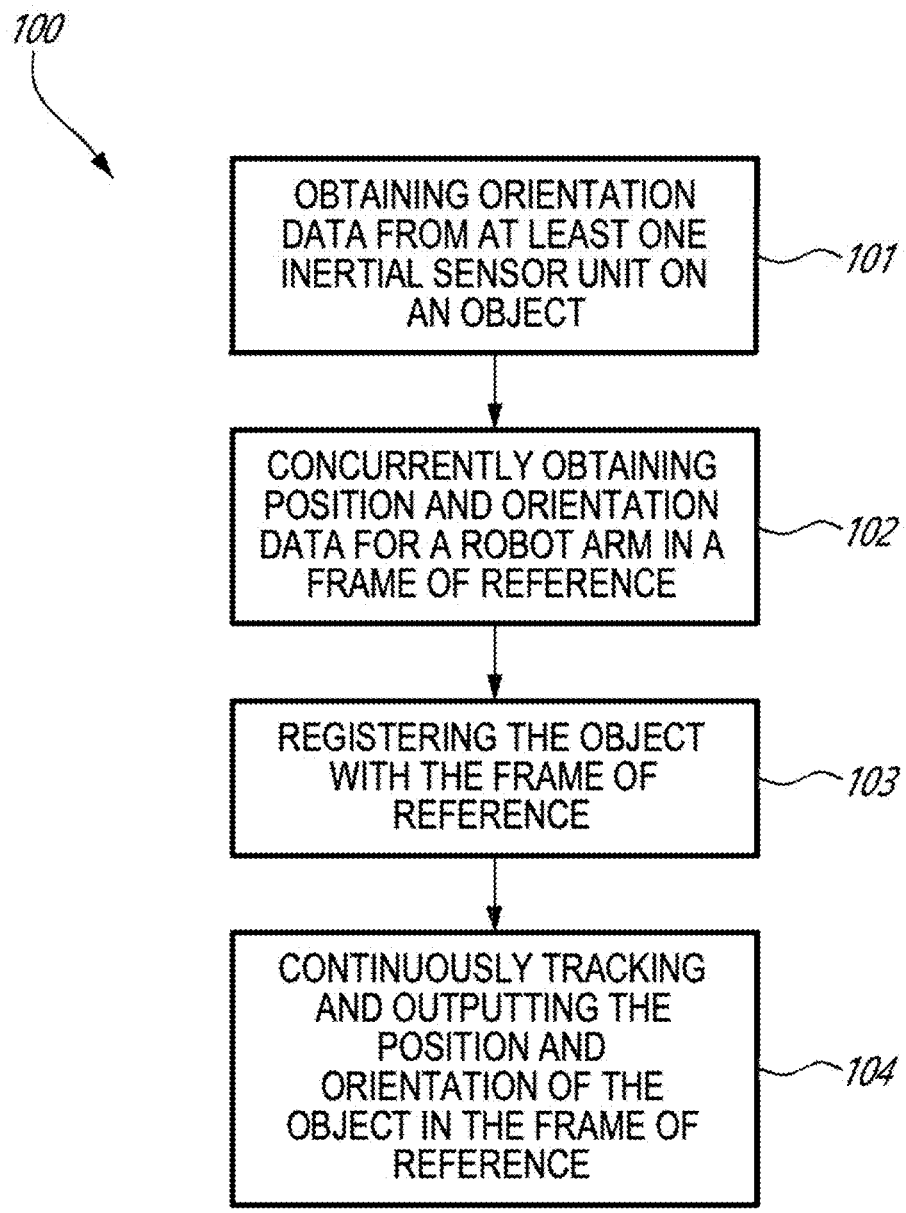
FIG. 3 is a flow chart of a method for tracking objects in robotized computer-assisted surgery in accordance with another aspect of the present disclosure.

Now that the various components of the tracking system 10 have been described, a contemplated procedure performed with the tracking system 10 or with a similar CAS system is set forth, with reference to FIGS. 1 and 3. The procedure shown in an exemplary embodiment is a resection of the femur at the knee. In FIG. 1, a contemplated use of the tracking system 10 is shown, as occurring during a bone model procedure in simulated surgery, between femur and tibia, for ease of visual representation. However, the contemplated use may be on real-life scenarios with patients being treated in orthopedic surgery, or other types of surgery.

A flow chart illustrative of a method for tracking objects is shown at 100 in FIG. 3, and is an example of a procedure that may be performed by the tracking system of the present disclosure. According to step 101, orientation data is obtained from the inertial sensor unit 30 on the femur. The orientation data may be indicative of an axis of the femur, such as the mechanical axis. Other data that may be tracked may include other axes, such as the medio-lateral axis of the femur, the frontal plane of the femur, a bone model of the femur, etc. In a variant, substeps are performed as part of step 101 to create the axes or other landmarks. For example, the mechanical axis may be determined using the method described in U.S. Pat. No. 9,901,405, incorporated herein by reference. If an additional inertial sensor unit 30 is required on the bone, it may be used. Accordingly, as per step 101, orientation data for the femur may be obtained from the inertial sensor unit 30. The orientation data may include one or more axes, one or more planes, landmark orientation, bone model associated with the axes, etc. However, in an embodiment, the inertial sensor unit 30 does not provide positional data.

In the example of the femur, it may be assumed that any movement of the femur is a rotation relative to the acetabulum, in instances in which the femur remains attached to the pelvis, e.g., no dislocation or prior to dislocation. Therefore, any angular change from the inertial sensor unit 30 may be indicative of a rotation of the femur relative to the pelvis. Whether the patient is in lateral decubitus or in supine decubitus, the mid-section weight of the patient may limit translation movement of the pelvis, and hence constrain the femur to be moved strictly in rotation relative to the pelvis. Various attachment devices, such as straps, belts, weights, etc, may be used to immobilize the femur and/or the pelvis. While the method is described for the femur, a similar procedure may be used for other bones, such as the tibia, the humerus, the spine, etc. For the tibia, an assembly as described in U.S. Pat. No. 10,729,452 may be used, the contents of U.S. Pat. No. 10,729,452 being incorporated herein by reference. Attachment devices may be used to immobilize such bones, and/or the attachment devices may constrain the bone to rotational movements, or may immobilize the bone, for example after axes and/or planes have been created for the bone or other object. The objects may also include tools.

As per step 102, position and orientation data for the robot arm 20 may be obtained, relative to a frame of reference. In an embodiment, the frame of reference is arbitrary, and fixed in space, as is the base 20A of the robot arm 20. The frame of reference may also be on the effector end of the robot arm 20, and move therewith. In a variant, the position and orientation data for the robot arm 20 is obtained from the sensors 25 embedded in the robot arm 20. A calibration may be performed by having the robot arm 20 contact fixed points (e.g., on the base of the robot arm 20), which fixed points could be reused during the operation for recalibration. The position and orientation data may be obtained from the robot driver 70, either alternatively or additionally. The position and orientation data may be for any part of the robot arm 20, including the end effector, the tool head 23, the cutting guide 24 thereon. In an embodiment, the robot arm 20 is the CMM reference for tracking, due to the precision and accuracy of the sensors 25. The robot base 20A could also be the CMM reference for tracking.

As part of the position and orientation data obtained in 102, an inertial sensor unit 30 on the robot arm 20 may also provide signals indicative of the orientation of the end effector, the tool head 23, the cutting guide 24. The orientation data from the inertial sensor unit 30 on the robot arm 20 may be optional, and may supplement the orientation readings calculated from the sensors 25 in the robot arm 20. Moreover, as detailed below, the inertial sensor unit 30 on the robot arm 20 may communicate with the inertial sensor unit 30 on the bone B, to exchange relative orientations with one another.

According to step 103, the object, i.e., the femur in the example, is registered with the robot arm 20, for the position of the femur to be known in the frame of reference tied to the robot arm 20. The registration may be known as a calibration, a handshake, a setting, an alignment. In an embodiment, the registration is achieved by a contact between the robot arm 20 and the femur, or between any object secured to the robot arm 20 and/or to the femur. For example, the robot arm 20 may have the cutting guide 24, an inertial sensor unit 30, or a probe in the tool head 23, among other possibilities, that may touch the inertial sensor unit 30 on the femur, the connector 32 supporting the inertial sensor unit 30, a cut guide (if present) or given landmarks on the femur. The contact between the robot arm 20 or component associated therewith, and the femur or component associated therewith, allows the tracking system to determine the instantaneous position of the femur, if the tracking system knows what the contact is. More specifically, the robot arm 20 may be controlled by the robot driver 70 or by the user in a collaborative mode, to cause a contact between cutting guide 24 and the pod 31 of the inertial sensor unit 30 on the femur. For example, a surface parallel to the guide surface 24A of the cutting guide 24 may be applied flat against a corresponding surface of the pod 31 of the inertial sensor unit 30 on the femur, in the instance where there is no cut guide on the femur. As the orientation of the femur is known relative to the inertial sensor unit 30 thereon, for example because of actions taken in step 101, the tracking system may determine the location of the femur (e.g., the mechanical axis thereof) in the frame of reference from the contact. This may entail a knowledge of the orientation of the pod 31 relative to the tracking data from the inertial sensor unit 30, and this data may be programmed or embedded in the inertial sensor unit 30. The contact may be a single surface-to-surface contact, a multipoint contact, etc. As another possibility, the robot arm 20, the cutting guide 24 thereon, or other component being registered in the frame of reference associated with the robot arm 20, may contact one or more landmarks on the femur, such as the condyles, the epicondyles, the posterior condyle line with a claw. Such a contact of bony landmarks may also occur after the registration, for instance to position a condylar plane relative to the frame of reference, and trackable via the inertial sensor unit 30. As another possibility, the camera 80, whose point of view is known in the frame of reference, images the end effector of the robot arm 20, and the bone with the inertial sensor unit 30 thereon. By image processing, the tracking module 60 may recognize the objects, and attribute a position and orientation to the objects using a known geometry of the objects (e.g., the models described above). For example, the tracking module 60 may be programmed with the geometry of a pod 31, and the images from the camera 80 (e.g., depth camera), may use appropriate techniques to determine the position and orientation of the pod 31 from its tracked point of view on the robot arm 20. Such appropriate techniques may include triangulation, model reproduction and mapping to existing virtual 3D model, and locating in the frame of reference.

Using the known location of the robot arm 20 from the sensors 25 (as CMM, or relative to a fixed point such as robot base), the bone may be located relative to the frame of reference. Accordingly, the camera 80 may be used punctually or instantaneously, to correlate the objects in the frame of reference. The camera 80 may be on the robot 20, or fixed relative to the robot, or on a head-mounted. Reference is made to co-pending application no. 63/185,528, incorporated herein by reference. The camera 80 may rely on room fixtures as suggested above, to add redundancy to the tracking, for example to confirm the tracking data, or to assist in determining movement of the robot base 20A.

The example above is for the femur, but similar approaches may be taken for other objects, such as the tibia B or surgical tools. In the case of the tibia, the inertial sensor unit 30 may be used in the manner described above for the femur, as an example. For a surgical instrument, a geometry of the instrument and the known relation between the instrument and the pod 31 may be used for the registration.

Calibration instruments may also be used as intermediary registration devices between the robot arm 20 and the object to be tracked. For example, a patient specific tool, for example manufactured using 3D printing or like manufacturing to be a negative surface of an object, may be used between the object and the robot arm 20 for the registration. For example, such tool may be on the end effector of the robot arm 20, and may couple to the object in a unique planned manner, for the contact handshake (which may be repeated after a time interval, when deemed necessary). Moreover, the registration may entail positioning and orienting the robot arm 20 relative to the bone without contact therebetween. For example, a non-contact pre-determined proximity relation between the robot arm 20 and the object may be replicated based on planning. If an inertial sensor unit 30 is on the robot arm 20 and another one is on the object, orientation data between the inertial sensor units 30 may be aligned in the frame of reference. Subsequent contacts may then occur for the object to be located in the frame of reference. Stated differently, the robot arm 20 is used as a CMM to locate the object or part thereof in the frame of reference used during the surgical procedure. Step 103 may be repeated as part of the method 100. For example, the step 103 may be repeated to register other objects, or to refresh or validation a previous registration. The repeat may occur just before alterations are made to the object, for example.

In step 104, after registration has been made, the object, e.g., the femur, is tracked continuously in position and orientation relative to the frame of reference associated with the robot arm 20. Concurrently, the position and orientation of the robot arm 20 may be tracked in the frame of reference, using for example the sensors 25 in the robot arm 20, and/or any other tracking technology on the robot arm 20. The continuous tracking of the object may rely solely on the orientation data from the inertial sensor unit 30 on the object, to determine its position and orientation in the frame of reference. This may be achieved by the absence of movement of the object, or because of its limited and constrained movement, tracked via the inertial sensor unit 30. In a variant, the orientation data from the inertial sensor unit 30 on the femur is obtained by the tracking system (e.g., the tracking module 60) and is monitored to update the orientation of the femur, as assumed to be fixed relative to its center of rotation at the acetabulum. If the tracking system observes an excessive movement, and/or if all inertial sensor units 30 produce a similar angular change signal, the tracking system may interpret this as a potential change of position of the femur in the frame of reference. As a consequence, a repeat of the registration as in step 103 may be performed. In an embodiment, the robot arm 20 has a cutting guide that is moved along the mechanical axis of the bone to position a cut slot relative to the mechanical axis. Item 80 may also be a light source emitting a light beam, that can be representative of the cutting plane. This may be a visual guidance for the operator or surgeon overlooking the scene.

The continuous tracking of the object, e.g., the femur, is output in any appropriate form. In a variant, a varus-valgus angle of an anticipated cut plane is output using the tracking of the cutting block 24 for the femur. In another variant, a display associated with the object, such as a bone model, axis, plane, is output as a result of the continuous tracking, relative to the robot arm 20 or tool supported by the robot arm 20 (e.g., cutting guide).

The two distinct sources of tracking data, i.e., the embedded tracking from the sensors 25 in the robot arm 20, and sourceless tracking from the inertial sensor units 30 providing an output associated to an orientation of the bones, ensure that sufficient tracking data is available for the tracking module 60 (FIG. 1) to determine a position of the bone B in the frame of reference. The tracking system and method described above may be without optical tracking technology, though optical tracking technology may also be present. The expression "without optical tracking technology" may in particular mean that no passive trackers are required, such as retroreflective element on a hard mount that is attached to the bones (often screwed to the bone). As set out above, the camera 80 may provide a visual feed that may be redundant. In a variant, the camera 80 is a depth camera that does not require such hard-mount passive trackers. To assist the camera 80, small tokens may be present, such as QR code tokens, or tokens with recognizable patterns. However, such tokens may not be invasive, by being adhered to surfaces, or with staples or the like that slightly penetrate the surface of the objects.

The present disclosure refers to the system 10 as performing continuous tracking. This means that the tracking may be performed continuously throughout the surgical workflow, or during discrete time periods of a surgical procedure. Continuous tracking may entail pauses, for example when the bone is not being altered. However, when tracking is required, the system 10 may provide a continuous tracking output, with any disruption in the tracking output triggering an alarm or message to an operator.

Now that a general procedure has been described, a particular procedure pertaining to surgery on bones that may not have substantial surface exposure, such as the pelvis. More particularly, during hip surgery, only a limited part of the pelvis may be exposed and visible. For example, the acetabulum and its rim may be the only visible parts of the pelvis. Due to this limited surface of exposure, it may be problematic to attach an inertial sensor unit 30 directly on the pelvis without substantial soft tissue disruption, though possible in some instances. Moreover, while in some patients some pelvic landmarks may be close to skin and thus palpable, such as the iliac spines, in many specimens the skin and other soft tissues may be too thick to serve as attachment landmarks for the pelvis. Also, unlike long bones that may be maneuvered to determine a location of the axes, the pelvis may not have this capability. However, if the anterior superior iliac spines protrude and are palpable, the pelvis may be registered in the referential system using a pelvic digitizer, such as described in U.S. patent application Ser. No. 17/126,090, filed on Dec. 18, 2020, the contents of which are incorporated herein by reference.

During the reaming of the acetabulum and the subsequent impacting of an implant, the orientation of the tool and cup implant may have an impact on the success of the surgery. The reaming and the impacting are typically done as a function of the anteversion and of the inclination of the femur, and hence the reaming and/or impacting may be done so as to orient a cup central axis in terms of anteversion and inclination. Accordingly, in such surgical steps, the surgeon, robot, or any operator may benefit from navigation data pertaining to an orientation of the pelvis, as the orientation of the pelvis may be tied to the precise reaming and/or impacting in the acetabulum.

In a variant, ultrasound tracking technology may be used to track the position and orientation of the pelvis. Referring to FIG. 2, an ultrasound imaging system 90 may be used to produce a signal indicative of at least one spatial and/or dimensional characteristic relating to biological tissue, such as the pelvis. According to conventional ultrasound-based detection principles, which are typical to conventional ultrasound probe units, an ultrasound emitter may be used to cast a sound wave and, upon an object being located within range of the ultrasound emitter, an echo of the sound wave is cast back to be sensed by an ultrasound sensor. In some embodiments, the ultrasound emitter and the ultrasound sensor may be separate from one another. However, in some other embodiments, the ultrasound emitter and the ultrasound sensor may be combined to one another in an ultrasound transducer performing both the ultrasound emission and the sensing functions. The echo may materialize upon the sound wave traveling through a first medium, such as skin, reaching a second medium of greater density compared to that of the first medium, such as a bone. As the speeds at which the sound waves may travel through various media depend on the respective physical properties of such media, characteristics of the echo (e.g., time elapsed between emission of the sound wave and the sensing of the echo, intensity of the echo relative to that of the sound wave, etc.) may be used to derive certain characteristics of the media through which the echo has traveled. In some embodiments, the functions of both the ultrasound emitter and the ultrasound sensor are performed by one or more ultrasound transducer transducers. In some embodiments, the ultrasound transducer may have one or more piezoelectric crystals emitting ultrasound signals based on corresponding electrical signals, and/or generating electrical signals based on received ultrasound signals. Any suitable type of ultrasound transducers can be used including, but not limited to, piezoelectric polymer-based ultrasound transducers such as poly(vinylidene fluoride)-based ultrasound transducers, capacitive ultrasound transducers, microelectromechanical systems (MEMS) based ultrasound transducers and the like.

Per the present disclosure, namely, in the exemplary case of orthopedic pelvic surgery, the ultrasound imaging system 90 may be configured to produce a signal indicative of a detailed spatial relationship between an ultrasound probe unit 91 (FIG. 4) and the pelvis, and also between soft tissue (e.g., skin, flesh, muscle, ligament) and the pelvis. Resulting datasets may include a contour of the pelvis, such as a periosteal contour associated to the pelvis. The resulting datasets may also include measurements of thicknesses, surfaces, volumes, medium density and the like. Advantageously, updated signal production via the ultrasound imaging system 90 and ad hoc, quasi-real-time processing may produce datasets which take into account movement of the pelvis. The ultrasound imaging system 90 may also include a dedicated computing device configured for conditioning and/or digitizing the signal, though it may also be a part of the CAS controller 50.

In some implementations, the ultrasound imaging system 90 may be suitable for producing a signal indicative of surfacic, volumetric and even mechanical properties of the pelvis to be tracked by the system 10. This may be achieved, for instance, by way of a multi-planar ultrasound system capable of operating simultaneously along multiple notional planes that are spaced and/or angled relative to one another, coupled to the CAS controller 50. Further, it is contemplated that other types of imaging systems, such as an optical coherence tomography (OCT) system, may be used in combination with the ultrasound imaging system 90. The type of additional imaging system may be selected, and combined with other type(s) as the case may be, to attain certain performance requirements in terms of effective range, effective depth, signal-to-noise ratio, signal acquisition frequency, contrast resolution and scale, spatial resolution, etc., among other possibilities. In some embodiments, partially exposed bone structures may be captured and/or referenced by the additional imaging system at any time before, during or after the surgery. Specifications of such imaging systems may thus be adapted, to some degree, based on requirements derived from typical characteristics of the objects O to be tracked.

Figure 4:
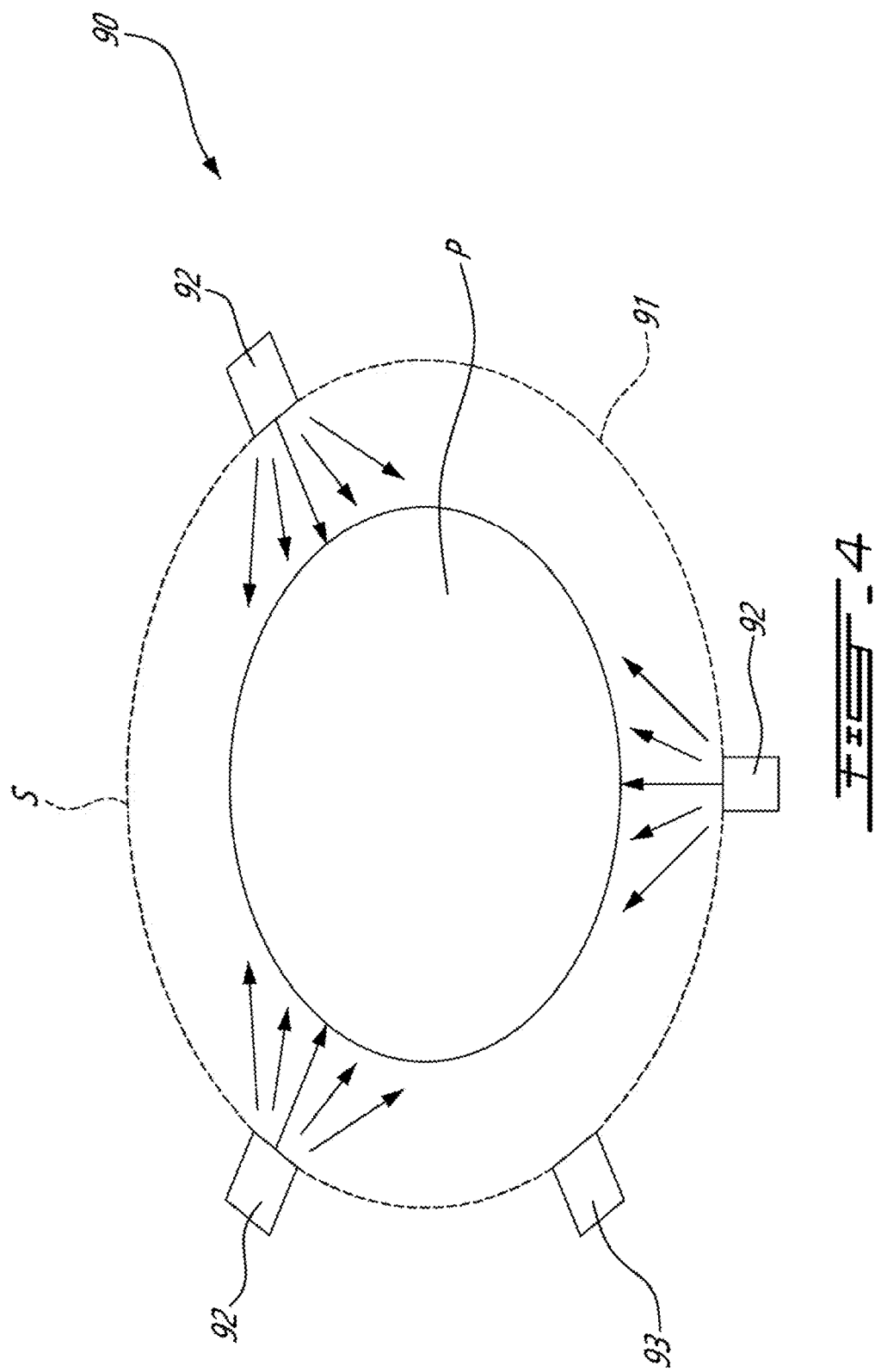
FIG. 4 is a schematic view of an ultrasound imaging system that may be used with the tracking system of FIG. 1.

According to an embodiment, with reference to FIG. 4, the ultrasound imaging system 90 is of the type that attaches to a body portion of a patient, and is used to track the pelvis. For this purpose, the ultrasound imaging system 90 has a wearable holder 91 and one or more ultrasound probe units 92, and may have another trackable reference such as an additional inertial sensor unit 93, though optionally.

The wearable holder 91 is of the type that is mounted about the outer-skin surface S (a.k.a., exposed skin, epidermis, external soft tissue, etc.) of the waist, covering the pelvis P. For example, the wearable holder 91 is a belt that can be tied to the waist so as to minimize movement between the ultrasound imaging system 90 and the pelvis P. The wearable holder 91 and the system it is part of, as will be described herein and as an example the ultrasound imaging system 90 of FIG. 2, may therefore be used to determine the position and/or orientation of the pelvis P. Accordingly, while portions of the pelvis P may be exposed during surgery, the pelvis P will otherwise remain substantially subcutaneous. While the pelvis P may be described herein as "underlying" the outer-skin surface S, it is to be understood that this does not exclude the possibility that certain portions of the pelvis, such as the acetabulum, will be exposed during surgery (e.g. by incisions, etc.).

The ultrasound imaging system 90 including the wearable holder 91 is configured to be secured to the waist in such a way that there is a no movement, or tolerable movement between the holder 91 and the pelvis. Algorithms can detect and compensate for movement using ultrasound processing. The ultrasound imaging system 90 is therefore a non-invasive tool to be used to track the position and the orientation, and thus the movement, of the pelvis through space before, before, during or after the computer-assisted surgery, for instance relative to the frame of reference described above.

Thus, the wearable holder 91 may essentially be a pressurized band or belt around the waist to enhance contact. It is also considered to use a gel conforming pad to couple the holder 91 to the skin, as a possibility. Traditional coupling gel can also be used. In some embodiments, coupling gel of typical formulations as well as biocompatible gel (e.g., in vivo biocompatible or in vivo bioexcretable) can be used. The gel conforming pad may include acoustically transmissive material which can help the transmission of the ultrasound signals and returning echo signals thereacross. The wearable holder 91 may thus be annular to surround the pelvis P.

Ultrasound probe units 92 are secured to the wearable holder 91. In an embodiment, the ultrasound probe units 92 include one or more transducers that emit an ultrasound wave and measure the time it takes for the wave to echo off of a hard surface (such as bone) and return to the face(s) of the transducer(s). In order to self-calibrate for the patient's individual speed of sound, some transducers are positioned accurately relative to others and as one emits waves, others listen and can compute the speed of sound based on well-known relative geometric positioning. Using the known speed of the ultrasound wave traveling through a bodily media, the time measurement is translated into a distance measurement between the ultrasound probe unit(s) 92 and the pelvis located below the outer-skin surface S. The transducers in the probe units 92 may be single-element or multi-element transducers, or a combination of both. For example, the probe units 92 may have multiple elements arranged in a phased array, i.e., phased-array ultrasound probe units 92, having the capacity of performing multi-element wave generation for sound wave direction control and signal reconstruction. In some embodiments, the phased-array ultrasound probe unit 92 has a single ultrasound transducer operating in a phased-array arrangement. When sensors are not rigidly linked to others, the relative position can be found with self-location algorithms. Therefore, the probe units 92 used in the manner shown in FIG. 4 produce signals allowing local image reconstruction of the bone. The phased-array ultrasound probe units 92 are configured to emit ultrasound signals successively towards different portions of the anatomical features. In some embodiments, the ultrasound signals may be successively steered from one portion to another. Alternatively or additionally, the ultrasound signals may be successively focused on the different portions of the anatomical feature. In another embodiment, the ultrasound probe units 92 are ultrasound devices integrated into the ultrasound imaging system 90. The measurement is done by either triggering it manually, or automatically. In one embodiment, the measurement is repeated at regular intervals. The measurements are constantly being transferred to the CAS controller 50 of the system 10 (FIG. 2), for the position and orientation of the pelvis in space may be updated.

The tracking of the ultrasound imaging system 90 in space may be done by a handshake with the robot arm 20, as described above. The tracking of the ultrasound imaging system 90 in space, combined to the image reconstruction data from the ultrasound probe units 92, is used to track the pelvis. For example, the image reconstruction from the signals of the ultrasound imaging system 90 may be used in conjunction with the bone models obtained by the system 10 to match or register the reconstructed image from ultrasound with the 3D bone models in the system 10, and hence position and orient the pelvis in the 3D space, i.e., the frame of reference. The registration may be performed automatically by the system 10. Stated differently, the CAS controller 50 may thus have the capability of mapping the ultrasound imaging to a pre-operative model of the pelvis P, in a registration of the live ultrasound imaging of the pelvis with the virtual model of the pelvis P, whether it be as 2D images or 3D model. An additional inertial sensor unit on the wearable holder 91, or at any other location related to the patient, can be used to monitor pelvis movement. The readings from such an additional inertial sensor unit may be interpreted to quantify the movement and/or to require an additional handshake calibration with the robot arm 20. The handshake calibration may be performed as a contact between part of the robot arm 20 and one or more of the ultrasound probe units 92. Alternatively or additionally, the camera 80 may register the ultrasound imaging system 90 in the frame of reference by visually recognizing one or more of the ultrasound probe units 92, through image processing.

The ultrasound imaging system 90 may thus be described as being an ultrasound tracking system for tracking a position and orientation of an anatomical feature(s) in computer-assisted surgery, such as the pelvis. The system 10 may include the ultrasound imaging system 90 having a phased-array ultrasound probe unit being adapted for emitting ultrasound signals successively towards different portions of the anatomical feature(s), measuring echo signals returning from said portions of said anatomical feature(s) and generating respective imaged echo datasets. The robot arm 20 may also be used to position the ultrasound phased array probe unit during the measuring, and generating corresponding coordinate datasets. The ultrasound imaging system 90 may be as described in U.S. patent application Ser. No. 17/206,552, filed on Mar. 19, 2021 and incorporated herein by reference.

Figure 5:
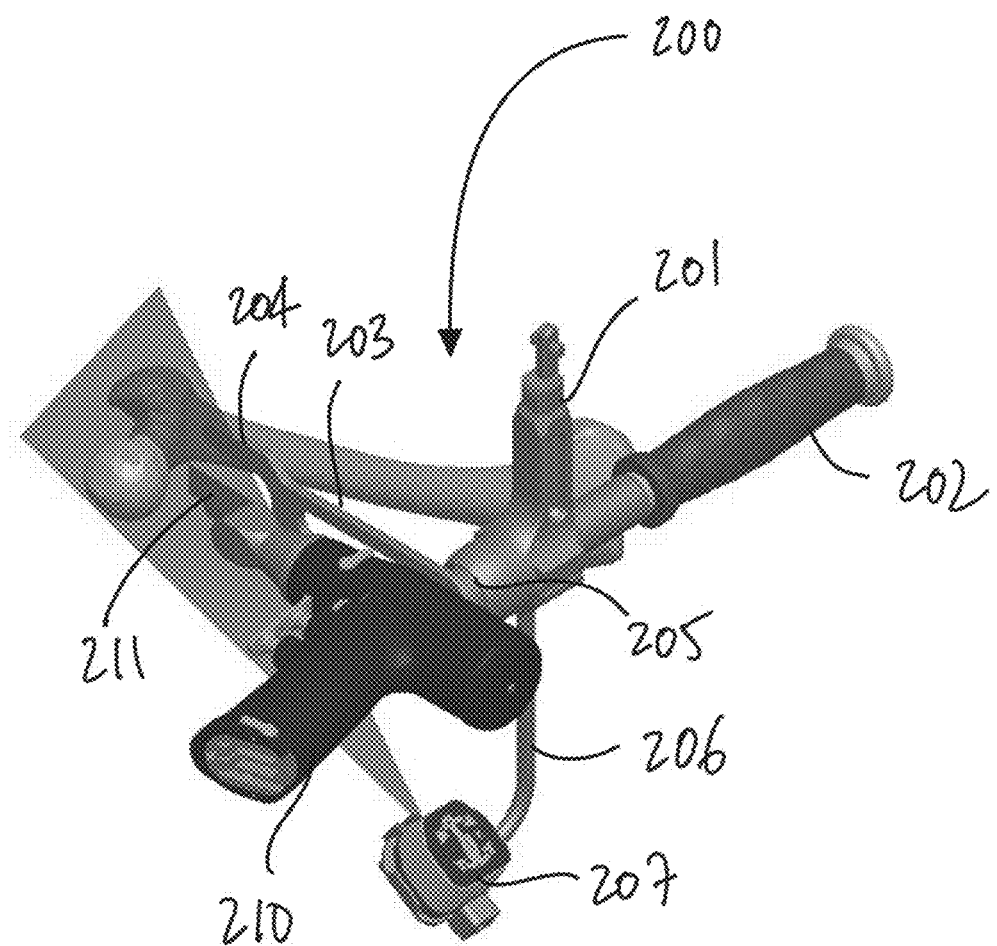
FIG. 5 is a perspective view of a tool assembly for resecting a femoral head that may be used during hip surgery, in accordance with the present disclosure.

In some types of hip surgery, it may be required that the femur be resected for a femoral implant to be inserted in the intramedullary canal. An exemplary tool assembly that may be used for resecting the femoral neck is shown at 200 in FIG. 5. The tool assembly 200 may be of the type handled by the robot arm 20, and may thus have a robot coupler 201, that is configured to be connected to the end of the robot arm 20 in a known manner. The tool assembly 200 may further have a handle 202 that projects from the robot coupler 201. The handle 202 may be optional, for instance considering that the robot arm 20 may be fully autonomously moved, without collaborative mode. However, an operator may prefer handling the robot arm 20 during resection, whereby the handle 202 may be present. The tool assembly 200 may also have a cutting tool mount 203, that may have any appropriate shape for connection of a cutting tool. In a variant, the cutting tool that is mounted to the cutting tool mount 203 may be aligned therewith in a predetermined manner, whereby the cutting tool mount 203 must be configured for such connection. As shown, the cutting tool mount 203 may have a slot that may be used as support for brackets, etc. A fork-like support 204 may be at an end of the cutting tool mount 203, or at any other location of the tool assembly 200. The support 204 is shaped to as slide onto the femoral neck, or other part of the femur, so as to provide a connection that may remove any play. Stated differently, the fork-like support 204 may contribute to removably anchoring the tool assembly 200 to the femur during the resection, in opposition to the forces of the cutting tool. The expression "fork-like support" describes the fork-like nature of the support 204, but the support 204 may have other configurations or may be referred to using other monikers, such as a U-shape support. As a possibility, the support 204 may be a C-shaped support, an L-shape support, or may have a clamp, a patient-specific shape (obtained via imaging), for connected to the femur. In a variant, an orientation of the support 204 may be adjusted, via lockable rotational joint 205. The lockable rotational joint 205 may provide a single rotational degree of freedom, or more if desired. An arm 206 may also project from the robot coupler 201, or from other part of the tool assembly 200. The arm 206 may be used to support a light source 207 emitting a light beam, such as a flat light beam as shown, that can be representative of the cutting plane. The light source 207 may be part of a pod that may also feature an inertial sensor unit 30, the inertial sensor unit 30 contributing to the tracking of the robot arm 20. In an embodiment, the system 10 relies on a knowledge of the geometry of the tool assembly 200 and on the internal tracking of the robot arm 20 to locate itself. Moreover, as per the method 100 described herein, the femur may be tracked in any appropriate way. This may be a visual guidance for the operator or surgeon overlooking the scene. In a variant, as shown in FIG. 5, the light beam is aligned with a cut blade 211 of a cutting tool 210, hence a connection arrangement between the tool mount 203 and the cutting tool 210 is configured for such alignment. Thus, the tool assembly 200 is well suited to be used according to the method 100, and tracked according to the tracking techniques described herein, such as without optical tracking.

The tracking system 10 or parts thereof may generally be described as a system for tracking at least one object in computer-assisted surgery, including: a processing unit; and a non-transitory computer-readable memory communicatively coupled to the processing unit and comprising computer-readable program instructions executable by the processing unit for: obtaining orientation data from at least one inertial sensor unit on at least one object; concurrently obtaining position and orientation data for a robot arm in a frame of reference; registering the at least one object with the robot arm to determine a position of the at least one object in the frame of reference; and continuously tracking and outputting the position and orientation of the at least one object in the frame of reference, using the orientation data from at least one inertial sensor unit on the at least one object and the position and orientation data for the robot arm. In a variant, the system and related method may be operated or be performed without any assistance from optical tracking. In a variant, the system and related method may be operated or be performed entirely and solely with inertial sensor units and sensors of the robot 20.

EXAMPLES

The following examples can each stand on their own, or can be combined in different permutations, combinations, with one or more of other examples.

Example 1 is a system for tracking at least one object in computer-assisted surgery, comprising: a processing unit; and a non-transitory computer-readable memory communicatively coupled to the processing unit and comprising computer-readable program instructions executable by the processing unit for: obtaining orientation data from at least one ultrasound imaging system connected to at least one object; concurrently obtaining position and orientation data for a robot arm relative to a frame of reference; registering the at least one object with the robot arm to determine a position of the at least one object in the frame of reference; and continuously tracking and outputting the position and orientation of the at least one object in the frame of reference, using the orientation data from the at least one ultrasound imaging system on the at least one object and the position and orientation data for the robot arm.

In Example 2, the subject matter of Example 1 includes, wherein the computer-readable program instructions are executable by the processing unit for controlling the robot arm as a function of a position and orientation of the at least one object.

In Example 3, the subject matter of Example 1 includes, wherein the system performs the continuously tracking and outputting the position and orientation solely with sensors in the robot arm and the at least one ultrasound imaging system.

In Example 4, the subject matter of Example 2 includes, wherein the system performs the continuously tracking and outputting the position and orientation without optical tracking.

In Example 5, the subject matter of Example 1 includes, wherein concurrently obtaining position and orientation data for the robot arm relative to the frame of reference includes determining the position and orientation data for the robot arm from sensors in the robot arm.

In Example 6, the subject matter of Example 5 includes, wherein the sensors in the robot arm are joint sensors.

In Example 7, the subject matter of Example 1 includes, wherein registering the at least one object with the robot arm includes performing at least one contact handshake with the robot arm.

In Example 8, the subject matter of Example 7 includes, wherein the at least one contact handshake includes the robot arm contacting the at least one ultrasound imaging system on the object.

In Example 9, the subject matter of Example 7 includes, wherein the at least one contact handshake includes the robot arm contacting points on the object.

In Example 10, the subject matter of Example 9 includes, wherein the object is a pelvis.

In Example 11, the subject matter of Example 7 includes, wherein performing at least one contact handshake with the robot arm is repeated at a time interval.

In Example 12, the subject matter of Example 1 includes, wherein registering the at least one object with the robot arm includes obtaining live images of the object and processing the images of the object relative to the robot arm to register the object in the frame of reference.

In Example 13, the subject matter of Example 12 includes, wherein obtaining the live images includes obtaining the live images from a point of view on the robot arm.

In Example 14, the subject matter of Example 13 includes determining the position and orientation data for the point of view from sensors in the robot arm.

In Example 15, the subject matter of Example 1 includes, registering a preoperative virtual model of the object to the at least one object in the frame of reference.

In Example 16, the subject matter of Example 1 includes, registering a preoperative virtual model of the object to the at least one object in the frame of reference.

The invention claimed is:

1. A system for tracking at least one object in computer-assisted surgery, comprising:
a processing unit; and
a non-transitory computer-readable memory communicatively coupled to the processing unit and comprising computer-readable program instructions executable by the processing unit for:
obtaining orientation data from at least one inertial sensor unit on at least one object;
concurrently obtaining position and orientation data for a robot arm relative to a frame of reference;
registering the at least one object with the robot arm to determine a position of the at least one object in the frame of reference; and
continuously tracking and outputting the position and orientation of the at least one object in the frame of reference, using the orientation data from the at least one inertial sensor unit on the at least one object and the position and orientation data for the robot arm.

2. The system according to claim 1, wherein the computer-readable program instructions are executable by the processing unit for controlling the robot arm as a function of a position and orientation of the at least one object.

3. The system according to claim 1, wherein the system performs the continuously tracking and outputting the position and orientation solely with sensors in the robot arm and the at least one inertial sensor unit.

4. The system according to claim 1, wherein the system performs the continuously tracking and outputting the position and orientation without optical tracking.

5. The system according to claim 1, wherein concurrently obtaining position and orientation data for the robot arm relative to the frame of reference includes determining the position and orientation data for the robot arm from sensors in the robot arm.

6. The system according to claim 5, wherein the sensors in the robot arm are joint sensors.

7. The system according to claim 1, wherein registering the at least one object with the robot arm includes performing at least one contact handshake with the robot arm.

8. The system according to claim 7, wherein the at least one contact handshake includes the robot arm contacting the at least one inertial sensor unit on the object.

9. The system according to claim 7, wherein the at least one contact handshake includes the robot arm contacting points on the object.

10. The system according to claim 9, wherein the object is a bone.

11. The system according to claim 7, wherein performing at least one contact handshake with the robot arm is repeated at a time interval.

12. The system according to claim 1, wherein registering the at least one object with the robot arm includes obtaining live images of the object and processing the images of the object relative to the robot arm to register the object in the frame of reference.

13. The system according to claim 12, wherein obtaining the live images includes obtaining the live images from a point of view on the robot arm.

14. The system according to claim 13, further including determining the position and orientation data for the point of view from sensors in the robot arm.

15. The system according to claim 1, further including registering a preoperative virtual model of the object to the at least one object in the frame of reference.

16. The system according to claim 1, further including registering a preoperative virtual model of the object to the at least one object in the frame of reference.

17. A system for tracking at least one object in computer-assisted surgery, comprising:
- a processing unit; and
- a non-transitory computer-readable memory communicatively coupled to the processing unit and comprising computer-readable program instructions executable by the processing unit for:
  - obtaining orientation data from at least one ultrasound imaging system connected to at least one object;
  - concurrently obtaining position and orientation data for a robot arm relative to a frame of reference;
  - registering the at least one object with the robot arm to determine a position of the at least one object in the frame of reference; and
  - continuously tracking and outputting the position and orientation of the at least one object in the frame of reference, using the orientation data from the at least one ultrasound imaging system on the at least one object and the position and orientation data for the robot arm.

18. The system according to claim 17, wherein the computer-readable program instructions are executable by the processing unit for controlling the robot arm as a function of a position and orientation of the at least one object.

19. The system according to claim 17, wherein the system performs the continuously tracking and outputting the position and orientation solely with sensors in the robot arm and the at least one ultrasound imaging system.

20. The system according to claim 18, wherein the system performs the continuously tracking and outputting the position and orientation without optical tracking.

* * * * *